(12) United States Patent
Grajales

(10) Patent No.: US 11,582,338 B2
(45) Date of Patent: Feb. 14, 2023

(54) WORLDWIDE INDIRECT TO DIRECT ON-DEMAND EYE DOCTOR SUPPORT REFRACTION SYSTEM VIA A REMOTE ADMINISTRATION TOOL MOBILE APPLICATION ON ANY PORTABLE ELECTRONIC DEVICE WITH BROADBAND WIRELESS CELLULAR NETWORK TECHNOLOGY 4G ,5G , 6G OR WIFI WIRELESS NETWORK PROTOCOLS TO INTERCONNECT BOTH SYSTEMS

(71) Applicant: Willis Dennis Grajales, Little Elm, TX (US)

(72) Inventor: Willis Dennis Grajales, Little Elm, TX (US)

(73) Assignee: Willis Dennis Grajales, Little Elm, TX (US)

( * ) Notice: Subject to any disclaimer, the term of this patent is extended or adjusted under 35 U.S.C. 154(b) by 8 days.

(21) Appl. No.: 17/180,789

(22) Filed: Feb. 20, 2021

(65) Prior Publication Data
US 2021/0266390 A1 Aug. 26, 2021

Related U.S. Application Data

(60) Provisional application No. 62/982,040, filed on Feb. 26, 2020.

(51) Int. Cl.
*H04M 1/72* (2021.01)
*H04M 1/72412* (2021.01)
*G16H 40/67* (2018.01)
*G06F 21/60* (2013.01)
*G06F 3/0482* (2013.01)

(52) U.S. Cl.
CPC ...... *H04M 1/72412* (2021.01); *G06F 21/602* (2013.01); *G16H 40/67* (2018.01); *G06F 3/0482* (2013.01)

(58) Field of Classification Search
CPC ... H04M 1/72412; G16H 40/67; G06F 21/602
See application file for complete search history.

(56) References Cited

U.S. PATENT DOCUMENTS

2018/0070820 A1* 3/2018 Fried .......................... A61B 3/14

\* cited by examiner

*Primary Examiner* — Curtis B Odom

(57) ABSTRACT

The present disclosure describes clinical workflows, methods, and systems used to perform an indirect to direct subjective refraction to a patient with a mobile smartphone application that works as a encrypted remote administration tool in any portable electronic device and interconnect both systems via by 4G, 5G, 6G, or Wifi. According to various embodiments, an eye doctor may utilize a remote administration tool (RAT) or (RAS) remote access software application on a portable electronic device (PED) (smartphone, tablet, or laptop) to view and control the main control base (MCB) anywhere in the world to interconnect both systems. The eye doctor can perform an on-demand live subjective vision refraction via RAT technology. Furthermore, the eye doctor can control the (MCB) that can control, exam chair, digital phoropter, vision chart software, robotic phoropter arm, exam chair height, exam room lights, and near robotic chart arm anywhere in the world.

20 Claims, 14 Drawing Sheets

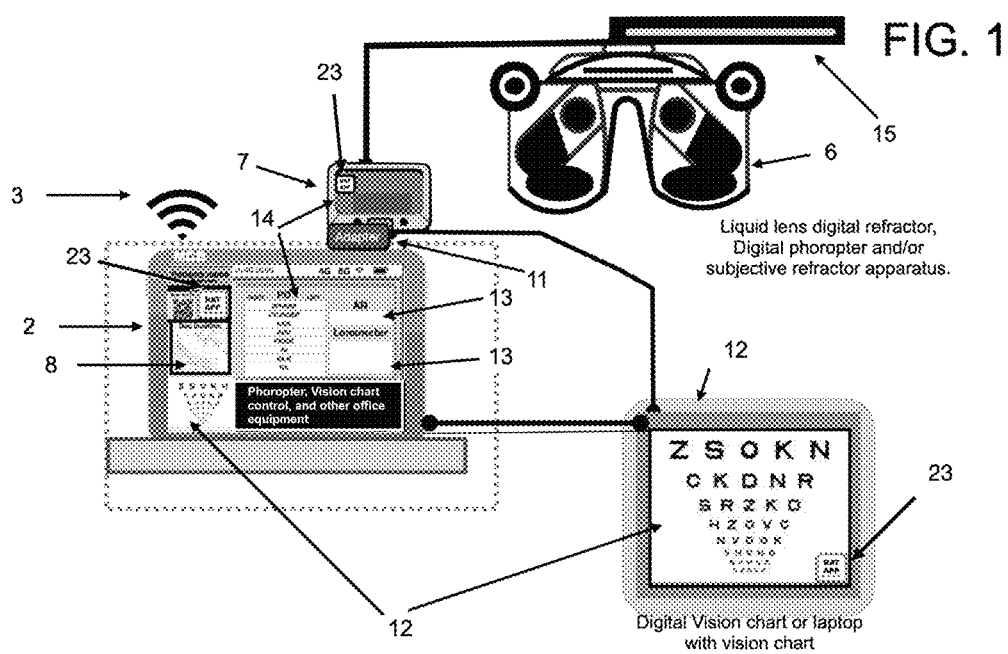

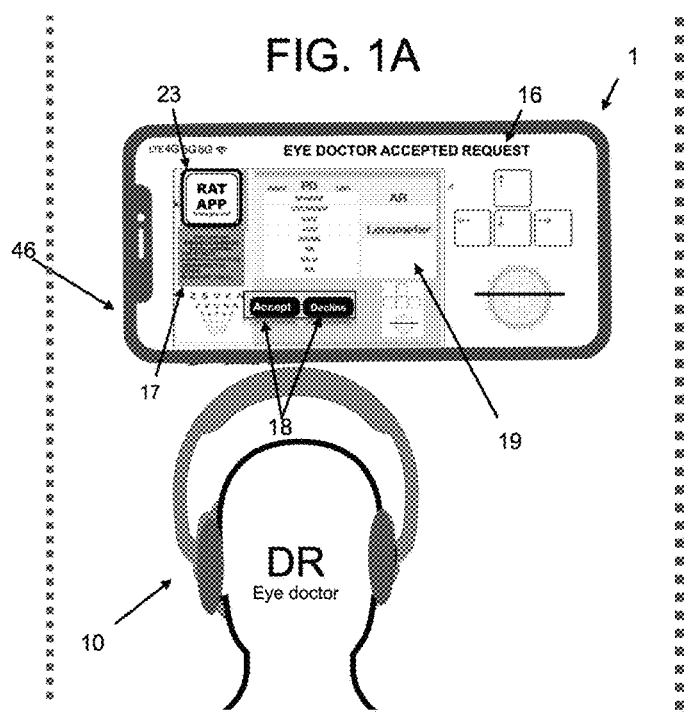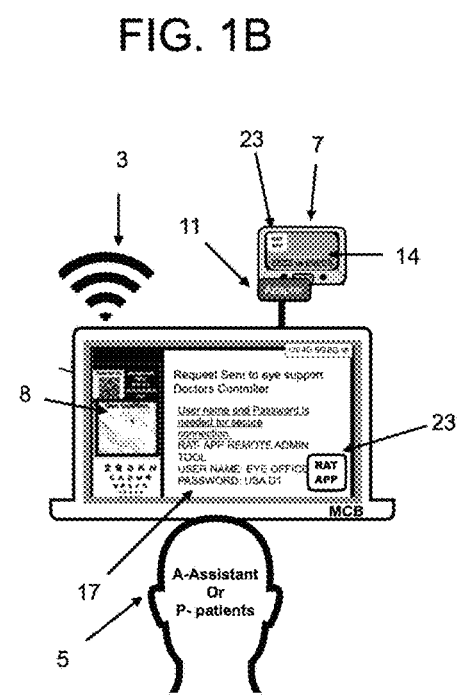

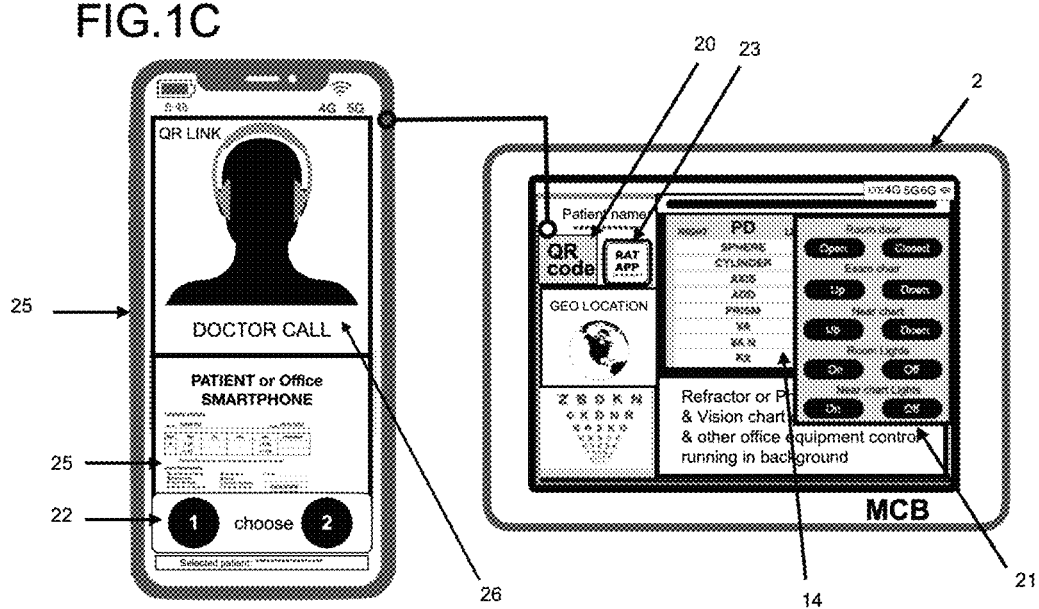

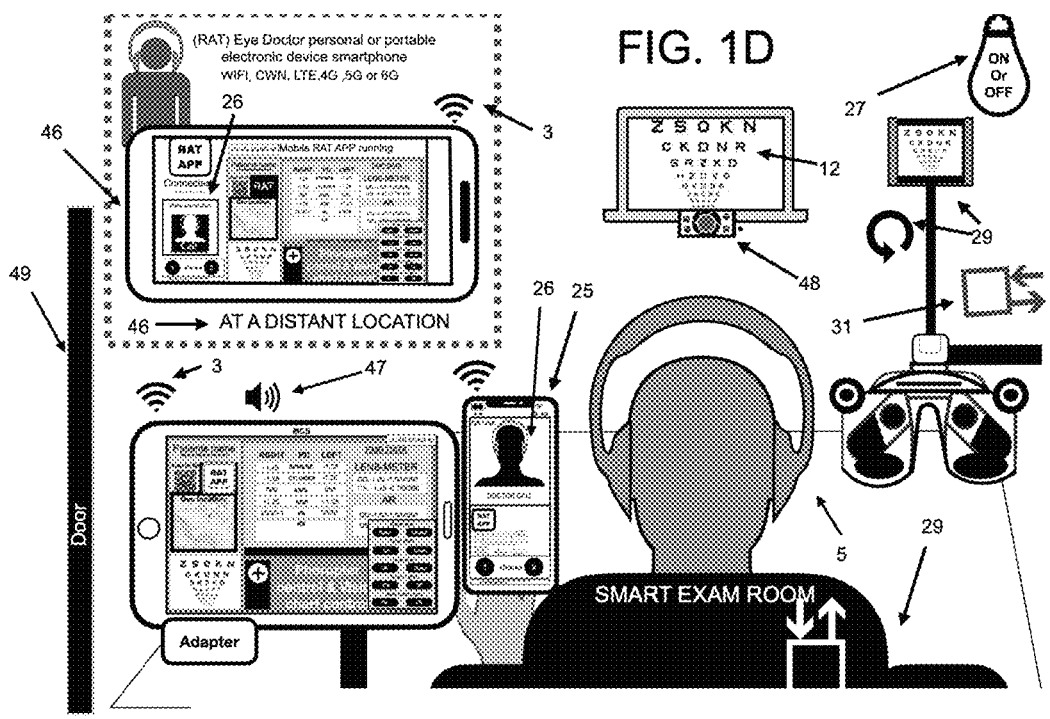

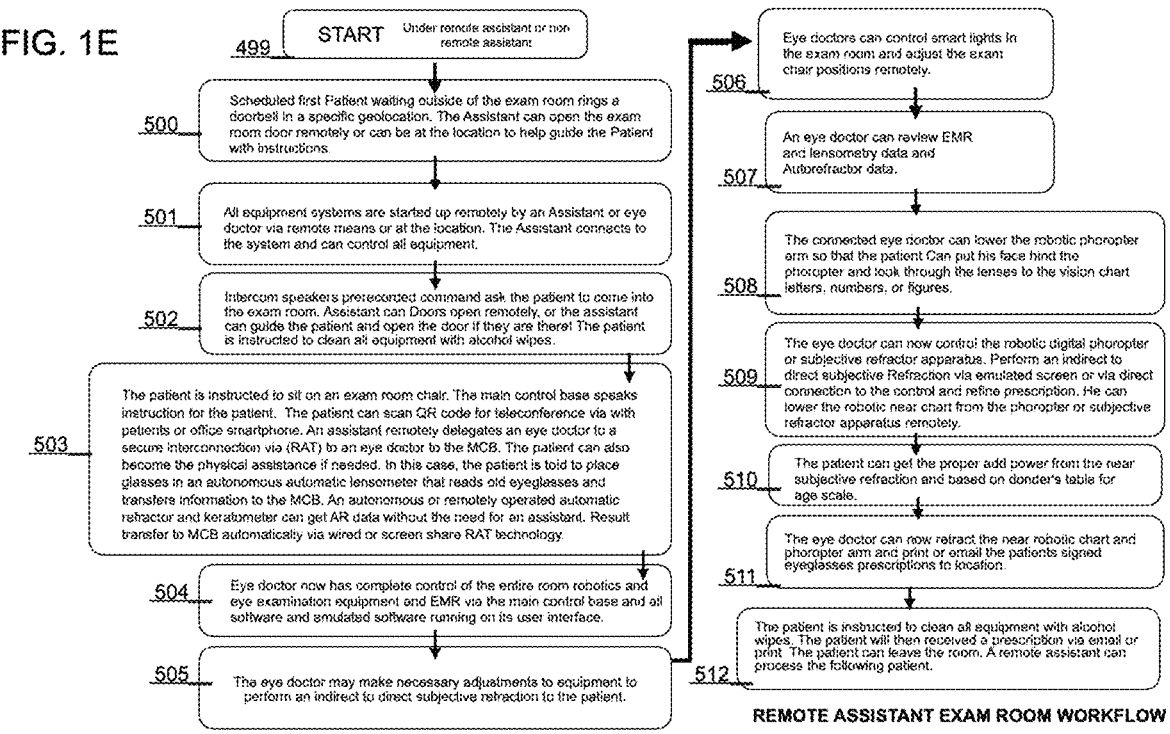

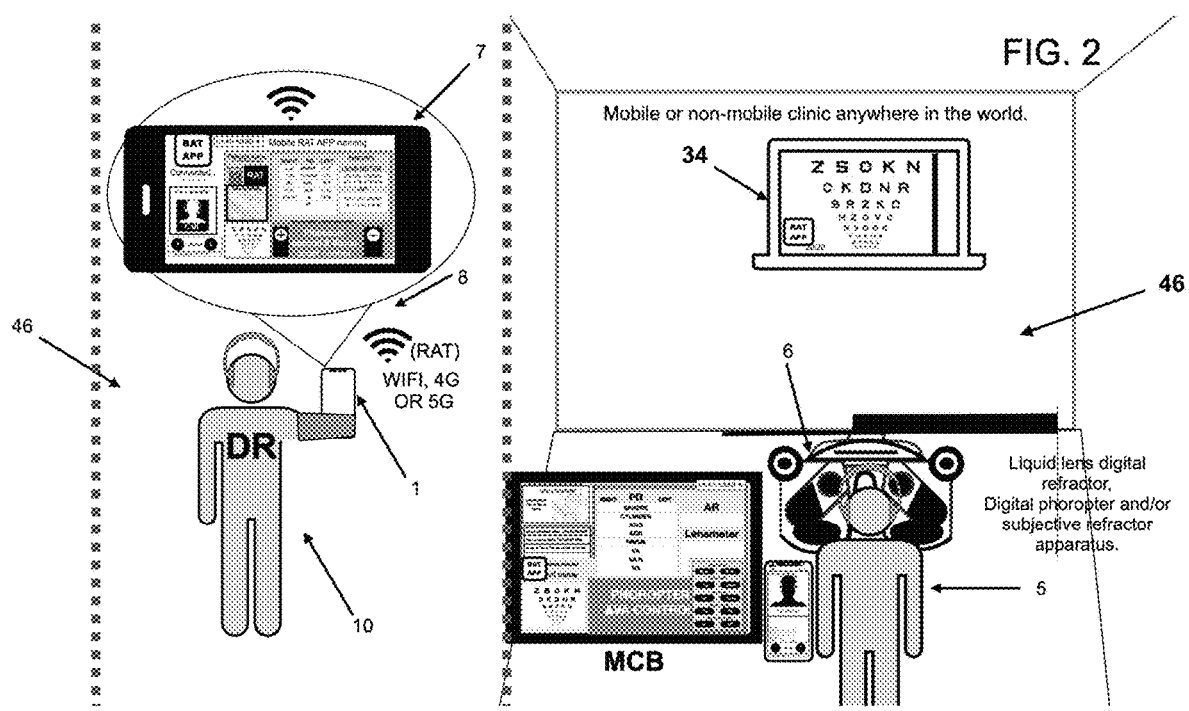

NON REMOTE ASSISTANT EXAM ROOM CONTROL EXAM ROOM WORKFLOW
RAT- A remote administration tool refers to any method of controlling a computer from a remote location also known as remote access software.

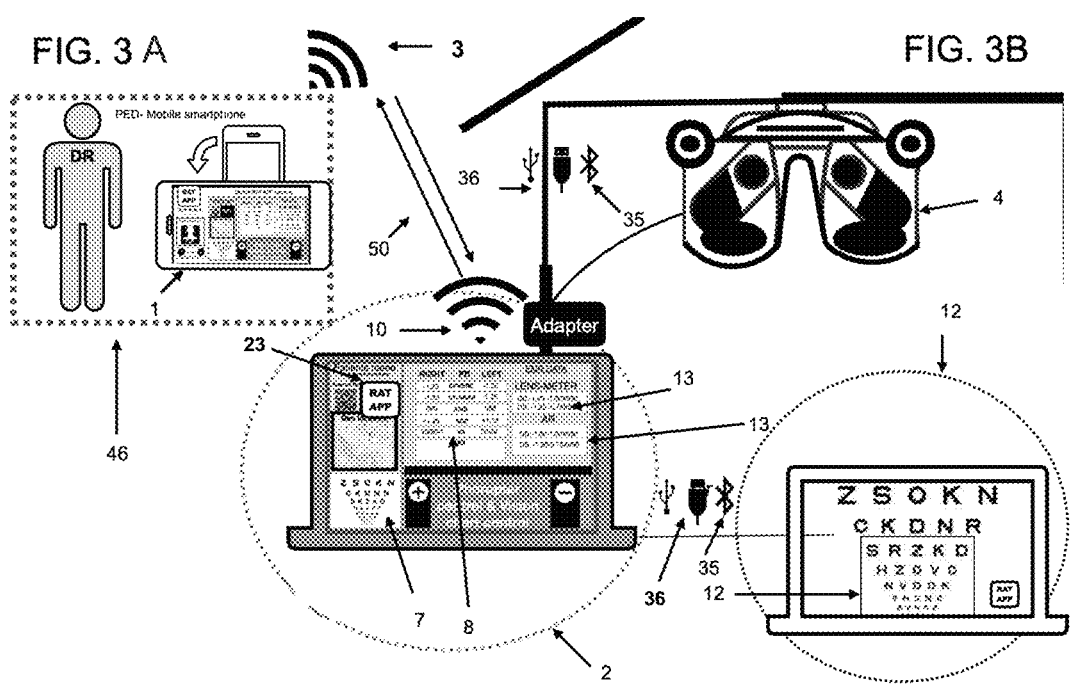

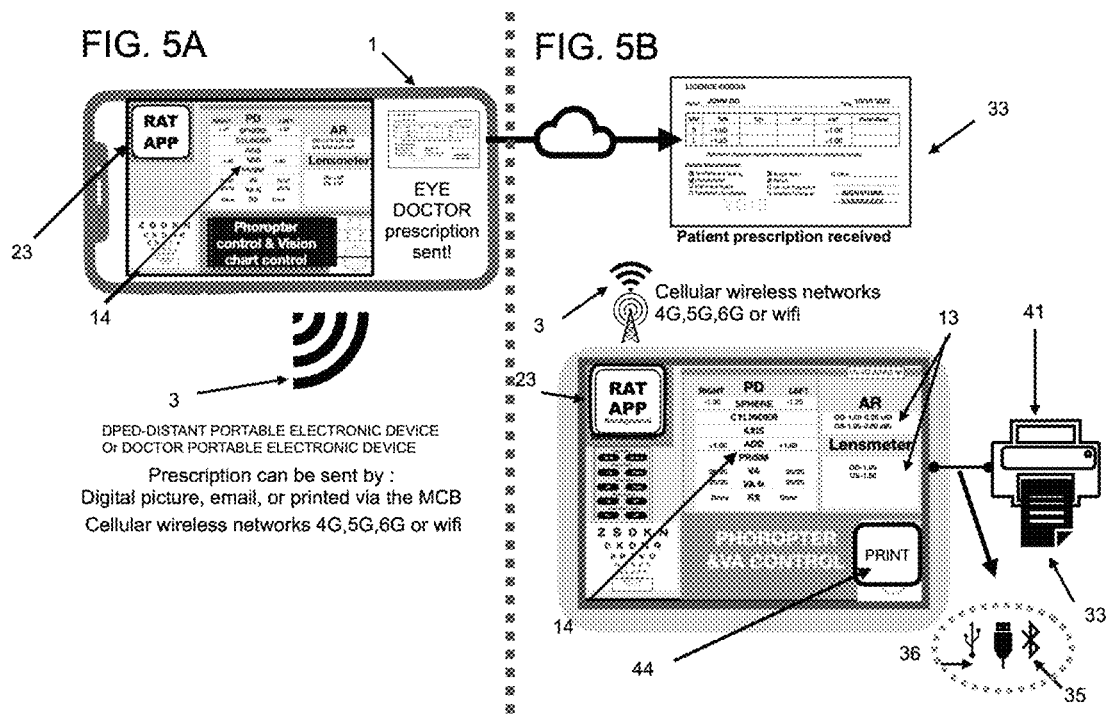

WORLDWIDE INDIRECT TO DIRECT ON-DEMAND EYE DOCTOR SUPPORT REFRACTION SYSTEM VIA A REMOTE ADMINISTRATION TOOL MOBILE APPLICATION ON ANY PORTABLE ELECTRONIC DEVICE WITH BROADBAND WIRELESS CELLULAR NETWORK TECHNOLOGY 4G ,5G , 6G OR WIFI WIRELESS NETWORK PROTOCOLS TO INTERCONNECT BOTH SYSTEMS

RELATED APPLICATIONS

This U.S. Patent Application is a continuation of U.S. Provisional Application No. 62/982,040 filed Feb. 26, 2020 titled "A indirect to direct on demand eye doctor support refraction system via Remote administration tool using any portable Digital Device by 4G, 5G or Wifi to interconnect both systems".

FIELD OF INVENTION

This disclosure relates to a clinical workflow, apparatus, method and system involving a robotic digital (phoropter and/or a subjective refractor apparatus), digital refractor device and/or exam room equipment that can be controlled by a main control base that is controlled by an on demand eye doctor with portable electronic device (PED) (smartphone, tablet, or laptop) via a mobile application to perform an indirect to direct subjective refraction service via 4G, 5G, 6G or WiFi interconnectivity in any mobile or non mobile vision exam room anywhere in the world.

SUMMARY OF INVENTION

In part, workflows, apparatus, method, and system of establishing interconnection via a mobile application that works as a remote administration tool. The interconnection is used to control and view the main control base. Which MCB and/or first or second computer system may controls many robotic medical eye examination equipment, devices and room equipment. Which method is provided via an emulated screens GUI, non emulated screens and RAT technology to provide indirect to direct on-demand eye doctor support refraction service with any portable electronic device via 4G, 5G, 6G wireless cellphone communication or Wi-Fi to a patient in an exam room. The exam room devices may be located in mobile clinic or a non-mobile clinic. The rooms may be located anywhere globally granted it may have wireless communication capabilities via broadband cellular network technology, CWN 4G, 5G, 6G, or.

This is not limited to accepting a first patient in an exam chair in a room including equipment and devices that may be remotely controlled. The MCB may be accessed by an eye doctor or assistant at or away from the location. The room may contain remote locks and doors that may be locked or open at the location or remotely. The room includes an exam chair that may be controlled remotely or not remotely. The room may contain one or more devices, robotic digital (phoropter or any subjective refractor apparatus) that may be controlled remotely or not remotely.

The room unit may include a mechanical lever that controls the near-reading chart of the (phoropter and/or subjective refractor apparatus). The room may contain a robotic (phoropter or subjective refractor) arm that can be positioned in front of the patient face safely. The room may contain lights that may be remotely controlled. The room may include a vision chart that can be a display or laptop running a vision chart software. The vision chart interface may be remotely controlled.

The room may include devices and equipment that may contain the ability to have broadband cellular network technologies, CWN 4G, 5G, 6G, or Wi-Fi internet capabilities, depending on location. The control of the exam room equipment may be possible by one or more software running on the main control base. The main control base may run secure password-protected EMR software, which may also be controlled. All data from auto-refractor readings and lensometry readings may also be viewed, emulated and/or controlled via the main control base. Only one patient data may be selected to be viewed at a time in each session. Since one or more of these equipment's and devices may be controlled by the main control base and therefore it may be reached by any (remote controller) eye doctor or assistant. The assistant, may be a (remote controller) if they are not able to make it to the exam location that day. The (controller) may be an assistant or an eye doctor.

The controller may be located anywhere in the world. The exam rooms and the patient may be anywhere in the world also. The (remote controller) may establish a connection to the main control base via a remote administration tool that interconnects both systems via any broadband cellular network technology 4G, 5G, 6G, or Wi-Fi, depending on equipment used. The controller may also ask the patient to be an assistant if needed in some cases since the main control unit system may be at arm's length from the patient. An eye doctor may control what may be viewed on the main control base by the patient.

Upon entering the room, the patient may view a QR code (FIG. 4B) on the main control base interface. The patient may scan the QR code with a smartphone camera app. The scan will establish a direct link to a web-based telemedicine connection that designates a secure video/audio, text or audio communication between the eye doctor or (controller) and patient. After the patient establishes video/audio, text or audio communication via smartphone, the patient can communicate with the eye doctor to begin the session. The eye doctor may answer any questions and gather the patient data, vision acuity, refraction vision choices before and during the subjective refraction via control of vision chart.

The eye doctor may conduct an Indirect to direct and/or direct to direct refractions to a patient. The eye doctor may perform at least one of a remote pupillary distance check, refraction and/or subjective refraction. During the session, the eye doctor (controller) may lower the (phoropter or subjective refractor) arm remotely. The eye doctor may ask the patient to position his or her eyes behind the digital (phoropter or any subjective refractor apparatus) and begin switching the powered lenses, and/or shape change focal lengths diopter power. The doctor may then provide a live refined subjective refraction session. The eye doctor may ask the patient which lens or focal length power choices they prefer to acquire the best eyeglass prescription.

Following the refined indirect to direct subjective refraction and/or direct to direct refraction completion, the eye doctor may sign an eyeglass prescription and print it remotely at the facility or send to patient's email.

BRIEF DESCRIPTIONS OF THE DRAWINGS

FIG. 1 Illustrates an example embodiment method, system, and apparatus connection of digital phoropter or digital liquid lens digital refractor connected to a computer system device where via an adapter, the information is emulated onto the MCB main control base computer system. The MCB is running multiple software and multi emulation software of equipment, and control softwares' and the mobile RAT application concurrently where it can be controlled by a remote eye doctor via a mobile application. The vision chart may be of any company brand or may be be a laptop with vision chart softwares running. Where the Vision chart laptop or computer display) may or may not have RAT app running within its user interface.

FIG. 1A and FIG. 1B Illustrate the embodiment of a request to accept or decline connection service from the on-demand eye doctor to the Main control base from an assistant or patient in the exam room. Where the eye doctor is in a distance or the same location running the RAT mobile application on his or her portable or personal electronic device. Where the eye doctor, when accepting, can view and control the main control base user interface (MCB) user interface on the Main control base to achieve indirect to redirect connection. Where in some instances, the eye doctor can connect directly to the medical equipment computer system via direct to direct connection via the RAT mobile application if needed, but most or all of the connections will be via the MCB connection via Indirect to direct.

FIG. 1C Illustration an example embodiment of what may be displayed on the main control base second computer system (MCB) and the patient or office smartphone after using the smartphone to scan a QR code on the MCB. Where the QR code may links to a video/audio, audio, or text message connection using the smartphone user interface via wireless internet interconnection to the eye doctor's personal or portable electronic device. Where the patient or office smartphone may be used to open an interactive application that can be used to choose lenses between one or two choices to refine the prescription on the digital phoropter or digital refractor apparatus. Where the MCB may also contains software emulated and/or non emulated on the screen that may control the exam chair height, lights, near robotic chart, robotic phoropter arm, digital phoropter, lens-meter and/or remote auto-refractor control apparatus.

FIG. 1D Illustration an example embodiment of a smart exam room setup. The patient is sitting in a remotely controlled exam chair that may be controlled by an on-demand eye doctor via the mobile application. The (controller) or eye doctor may control the remote auto-refractor system, the autonomous lens-meter, robotic near chart apparatus, the robotic phoropter arm, and the remote door locks. Where via a patient or office smartphone, a patient may communicate with the distance eye doctor or controller via wireless internet connection CWN, LTE, 4G, 5G, 6G or Wi-Fi.

FIG. 1E Illustration of an example of a workflow chart of a method for a remote or non-remote assistant via (RAT) to guide a patient into the exam room and provide instructions while also helping with the eye doctors interconnection to the system to provide an indirect to direct subjective refraction service.

FIG. 1F Illustrate a pictorial diaqram of how the remote administration tool interconnection from the eye doctor (PED) personal or portable electronic device computer system and the main control base computer system. Where the main control base (MCB) can emulate via an adapter and emulation software one or more user interfaces of the eye examination equipment computer system of the refractor, digital phoropter and/or digital variable liquid lens refractor or any digital subjective refractor apparatus and vision chart with vision chart software. Where the controller's PED can be a smartphone, laptop, tablet, and the MCB can be a laptop, smartphone tablet, or PC, where the PED and the MCB computers system may be any operating system Windows, IOS, Android, Linux, Chrome OS, or Raspberry PI OS.

FIG. 2 Illustrates an embodiment of what may be displayed in a mobile clinic or non-mobile smart eye exam room clinic and what is viewable by the a controller (eye doctor or virtual assistant) via remote administration tool application and the office MCB interconnection. The connection can be made via Wi-Fi, internet satellite, or cellphone wireless networks.

FIG.3 Illustrates a workflow diagram of a method to accept or decline a RAT interconnection from the eye doctor (controller) to the main control base (MCB) secondary computer system that emulated all office equipment controls and systems to provide an indirect to direct subjective refraction service. Where via the RAT connecting to the MCB, the eye doctor can send prescription information via the MCB to print at the remote location or send via email. The final connection delegates the second part of the examination to an on-site or offsite HCP, Ophthalmologist and/or Optometrist. All records (EMR) information may be stored at the remote location where the patient is being seen.

FIG. 3A and FIG. 3B Illustrates an embodiment of how the robotic digital phoropter or variable liquid lens focal length subjective refractor or subjective refractor apparatus may be controlled remotely via an adapter to any subjective refractor apparatus or software or phoropter computer system of any maker or model. Where the connection from the eye doctor to the first computer system or second computer system to the eye examination equipment may be via wire cable or Bluetooth, depending on the equipment used). Where via the adapter, any type of subjective refracting system and vision chart may be controlled remotely by a controller via the mobile application or software on all systems or without the need for software on all systems.

FIG.4 Illustrates an example embodiments of the main control base computer system at the remote examination location providing geolocation and a list of patient data displayed in the user interface. Where an eye doctor can view and check a patient scheduled at the location before or after providing eye examination service. Where the access, control, and viewing of the eye doctor to the MCB is based on a remote administration tool category technology application.

FIG. 4A and FIG. 4B Illustrates example embodiment of a setup where the assistant may be inside the room, and the patient's or office smartphone is connection with an eye doctor and may be miracast screen mirrored, or transmitted via wireless or non-wireless communication protocol to a laptop or smart display via wired HDMI, Bluetooth, or Wi-Fi. Where the patient has the choice of seeing the eye doctor via the laptop or smart display or via the smartphone. Where the patient is position receiving an (indirect to direct) subjective refraction using digital phoropter or variable liquid lens subjective refractor apparatus. Where the eye doctor can control some of the equipment in the exam room.

FIG. 5A and FIG. 5B Illustrates an example embodiment of a method of an eye doctor connected to the (MCB) main control base computer system connected to a network printer. The (controller and/or eye doctor) can print the new eyeglass prescription at the remote office via the mobile application, interconnecting both systems via screen mirror, screen share, and screen control.

Figure 6:
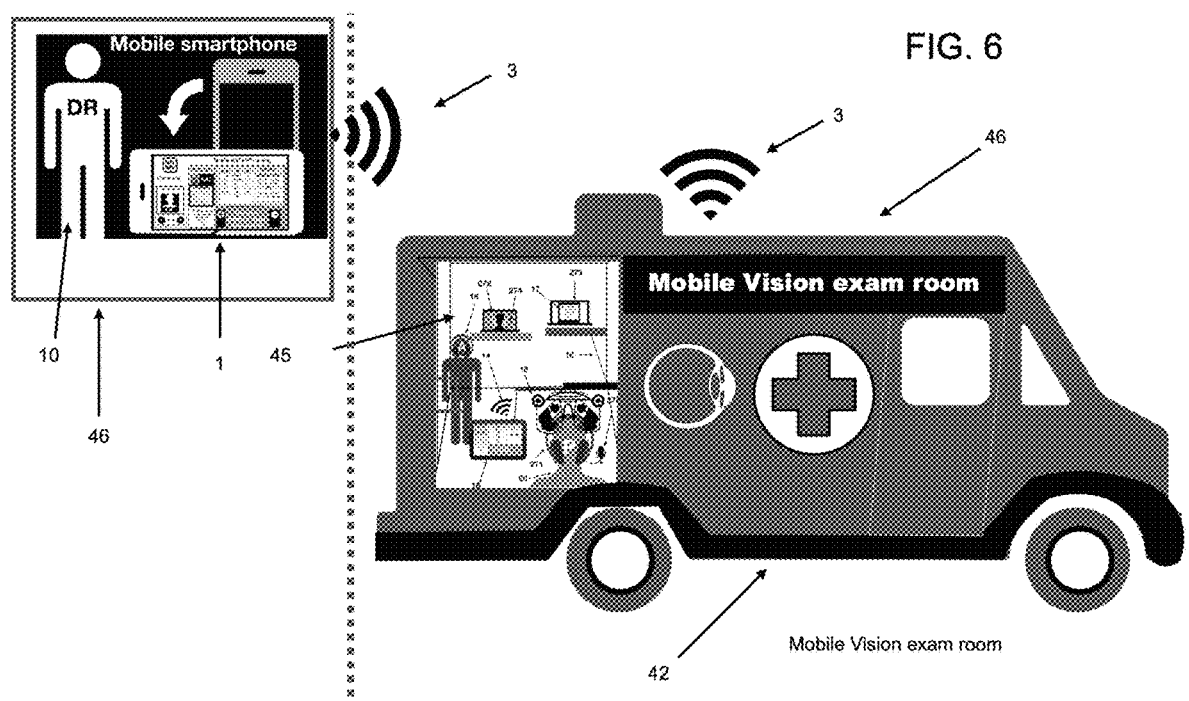

FIG. 6 Illustrates an example embodiment of a mobile clinic including a vision exam room inside a vehicle where the smart exam room equipment and/or devices may be controlled remotely by an eye doctors portable or personal electronic device (PED). Also, that a remote assistant or eye doctor may control the MCB to perform remote administration tool controlled subjective refractions services via Wi-Fi, Satellite internet, cellphone wireless networks, CWN LTE, 4G, 5G 6G, and/or any other next-generation wireless cellular network technology.

DETAILED DESCRIPTION

Many health practitioner facilities in the world are incorporating telemedicine technologies in their establishments. Some practitioners use telemedicine video/audio devices to connect with remote patients or other doctors to provide medical service too distant hospitals. This has become a new normal after the covid19 pandemic. For example, a remote radiologist may provide his medical service in a relatively large hospital in a city. This same radiologist may provide telemedicine video advice, viewing, consultation or assistance to patients and/or other medical professionals in a secondary hospital located in a remote area.

Some of these telemedicine encrypted video consultation services are provided by new companies that provide low-cost HIPAA, PIPEDA, and/or GDPR compliant video conferences to doctors and patients by just scanning link URL with no need to download software. Telemedicine systems are becoming normalized worldwide. However, the use of remote telemedicine robotics control is still in its infancy. Amazingly such robotic devices like the da Vinci surgical system is a robotic surgical system made by the American company Intuitive Surgical.

It is designed to help surgery using an remote controlled approach by a surgeon from a console. The da Vinci System consists of a surgeon's console typically in the same room as the patient or at a patient side cart with interactive robotic arms managed from the console. Just as these new robotic medical devices emerge the use of new innovative ways to provide medical service will emerge. Also new way to provide medical services at a global level will emerge.

The present disclosure provides various methods, system, apparatus, and clinical workflows in the field of telemedicine robotics to operate a one or more devices, robotic digital (phoropter 6, liquid lens subjective refractor 6 and/or subjective refractor apparatus 6) and other equipment in an exam room 46 (smart exam room) from a remote location. This system achieves this via indirect to direct means using a main control base computer system and/or a first or second equipment computer system with adapters 11 running, emulating software's 14 13, screen share 39 and remote administration tool software's to perform eye examinations multiple means using emulation software's. The following is for utilizing the main control base (MCB 2), a computer running on any operating system 24 and running multiple software, multiple emulators, emulating screens, and remote administration tool technology 23 to improve connection control and view to a controller 10 (eye doctor 10 or assistant 38). Interconnecting the office MCB 2 with the (controller 10) to provide an indirect to direct subjective refractions to a patient 5 via and mobile application that works as or with a remote administration tool 23.

In some situations the system may switch to a service sharing that may not provide direct service. Instead of providing the primary service, the system will instead provide a secondary eye doctor's 10 connection to connect and perform an indirect to direct refraction remotely. The new users or (controller 10) set up a personal profile with a name, phone number, state license number other information, and payment preference, which could be a credit card, e-commerce payment system or, in some cases, cryptocurrency address. This payment will be used to pay the independent contracted eye doctor 10 for the service provided 46.

Service may generally be accessed via one or more mobile applications. The application may ask to contain users (controller 10) set up a personal profile with a name, phone number, state license number other information, and payment preference, which could be a credit card, e-commerce payment system or, in some cases, cryptocurrency address, or e-cash. The remote administration tool 23 mobile application can be of commercial or non-commercial use. The Remote administration tool 23 application may be used on any portable electronic device via 4G, 5G, 6G or Wi-Fi 3 to interconnect both systems.

The robotic digital phoropter 6, liquid lens subjective refractor 6, subjective refractor apparatus 6, autonomous lens-meter, and/or auto refractor 48 system (FIG. 1D), and exam room 46 equipment (FIG. 1D) (FIG. 1) (FIG. 4B) may all be controlled remotely by a controller (eye doctor). The controller 10 may be an assistant, and/or eye doctor connected to the RAT app to controls the main control base MCB 2 that controls one or more equipment's and devices. As used herein, a telemedicine video interconnectivity via office smartphone 25 or personal smartphone 25 between the eye doctor 10 controller 10 and patient 5 in the eye exam room 46 is established via both the controller 10 and patient's 5 personal or portable electronic device PED 1. (FIG. 1D). The connection can also occur via live chat or an application; The controller may easily communicate with a patient 5 via text and/or screen sharing software technology.

A secured doctor to patient 5 indirect to direct subjective refraction peer to peer support service. This support service system allows subjective refined refraction to be made via at-least two mobile applications that work as remote administration tool 23 (RAT) or remote access software (RAS) (FIG. 1F) without the eye doctor 10 having to be in the exam room 46. The remote administration tool 23 software, emulating software's, screen mirroring software's, screen control and/or Remote access software (RAS) can be of commercial and/or of non commercial means. The eye doctor 10 can be on-site in different rooms 46 or off-site anywhere in the world 46. The patient 5 can be anywhere in the world 46 in a mobile or non-mobile exam room 46.

Figure 4:
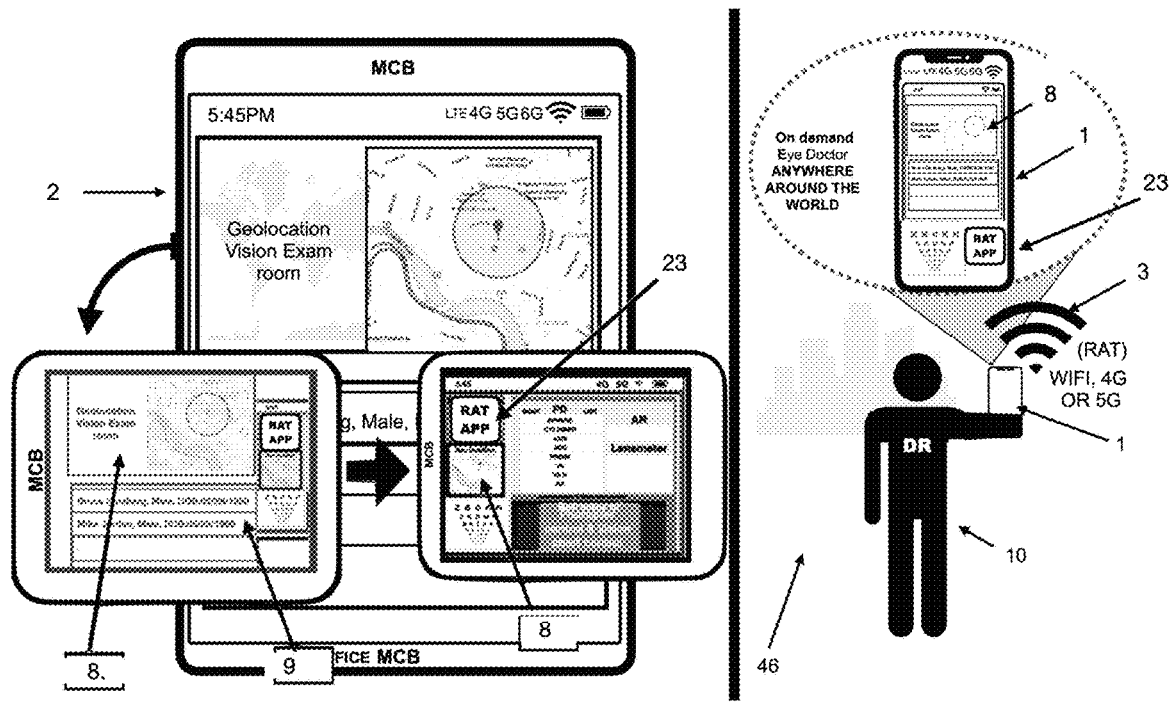
Figure 4A:
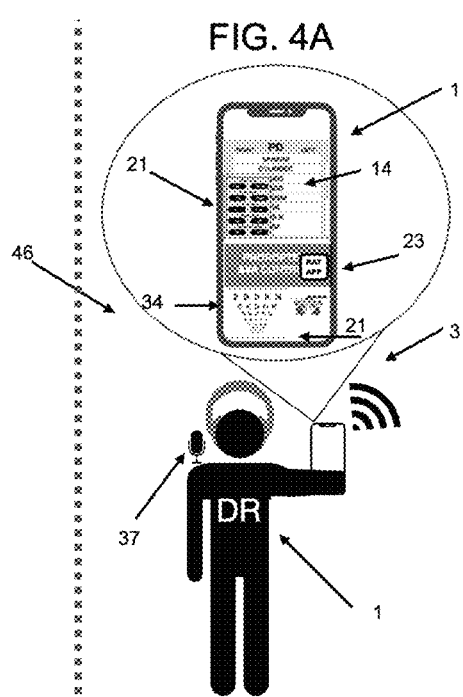
Figure 4B:
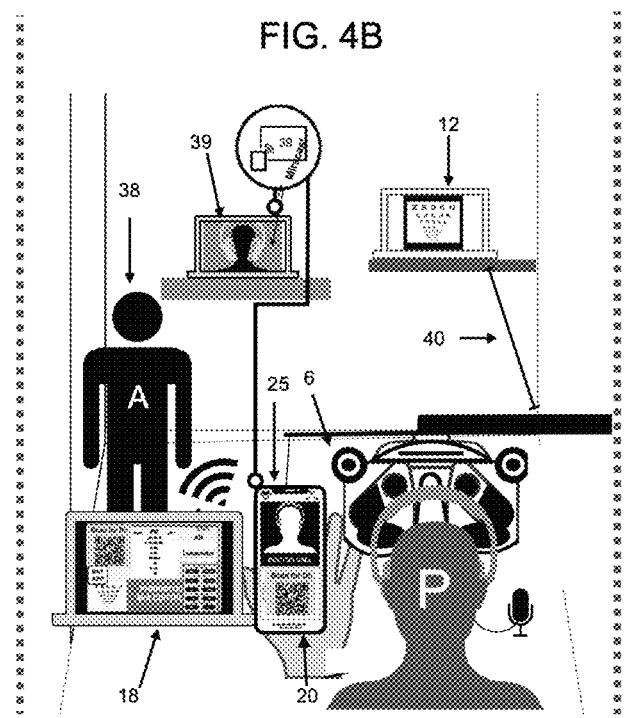

An example of an office inside a mobile clinic 42 or non-mobile clinic 46 location 8 is the following pictorial representation. (FIG. 6) (FIG. 4B). The exam location 8 46 main control base can be connected to an online medical appointment booking service 9 if needed. However, it may also have the possibility of using online medical appointment booking service 9 third party commercial or non-commercial with a patient 5 PED 1 app. The exam room 46 equipment door 49 28 and lights 27 can also be controlled via the RAT via the MCB 2 21.

Figure 3:
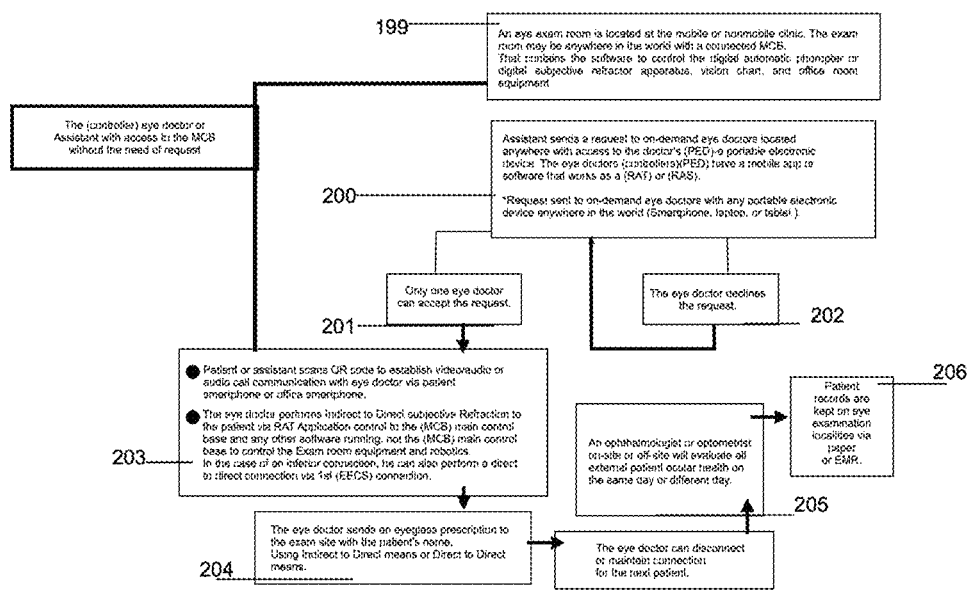

The support connection is made at least one (RAT or RAS) software or application via 4G, 5G, 6G CWN, cellphone wireless network or Wi-Fi 3. (FIG. 3A) (FIG. 3B). The robotic (digital phoropter 6 or liquid lens subjective refractor 6) and vision chart 34 (DP and VC) can be controlled directly by the MCB 2 by an assistant 38 in the office (FIG. 1F) via Bluetooth 35 or wired connection (FIG. 3B) depending on the system used. The MCB 2 may contain a universal adapter 11 that facilitates the control and connection to any digital (phoropter 6 or liquid lens subjective refractor 6) in the market to control the digital (phoropter 6 or liquid lens subjective refractor 6).

FIG. 1E illustrates examples embodiments of a situation where an assistant 38 may not be physically present during the service. Where the virtual assistant 38 may control the main control unit to communicate with the patient 5, open the door 28 49 remotely and virtually instruct the patient 5 to clean the equipment with alcohol wipes and sit in the exam chair 30 for the beginning of the session. The virtual assistant 38 may be able to ask the patient 5 to put his or her glasses in an automatic lens-meter that may acquire the eyeglasses prescription on a push of a button the lensometry reading of old glasses may be uploaded to the main control base 2 software 13 or may be viewed by an emulating software to the MCB user interface 2.

The virtual assistant 38 can also tell the patient 5 to situate him or herself in front of a camera that works like as a remote auto-refractor 48 and/or keratometer 48 both eyes will be scanned 45. The virtual assistant 38 may also tell the patient 5 to situate him or herself in-front of a secondary camera controlled remotely that works to find the patient 5 pupillary distance. The results may automatically be sent to the main control base. The virtual assistant 38 may then give access to the selected eye doctor 10 (username 17 and password 17) to control the main control base. The virtual assistant 38 may then tell the patient 5 to scan a QR code 20 43 to weblink (FIG. 1C)(FIG. 1D) on the main control base for the patient 5 to connect directly with the eye doctor 10 via the patient 5 PED 1 RAT mobile application.

Figure 1F:
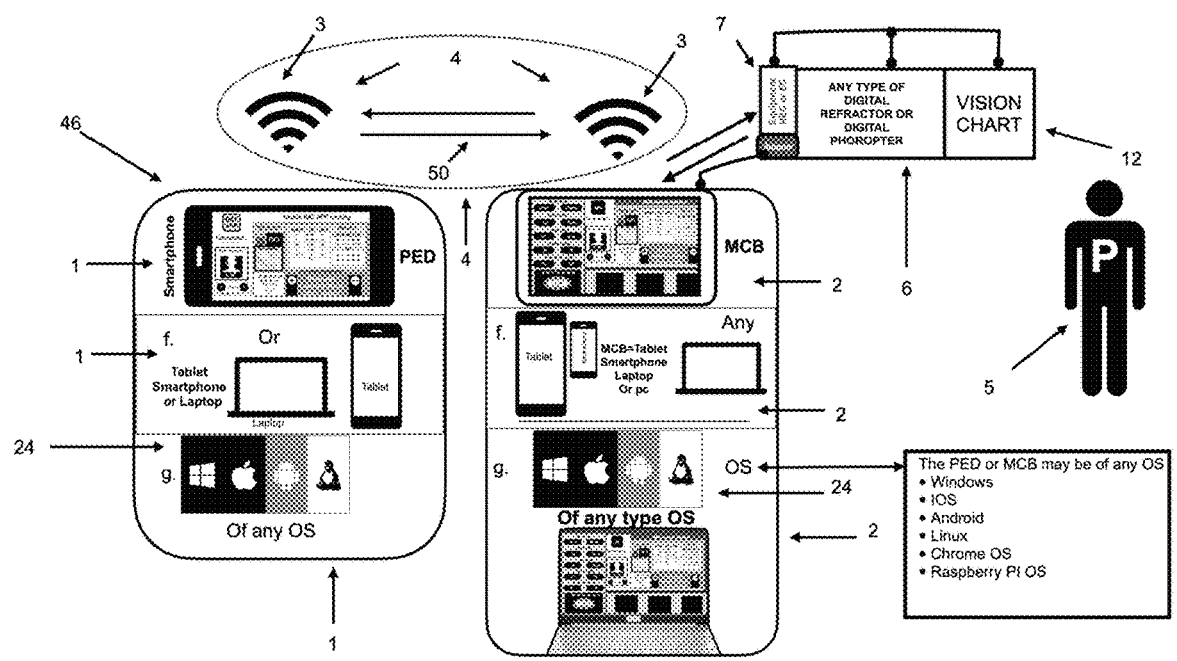

During this time, the eye doctor 10 may connect to the main control base and have full control of the smart exam room devices 46 and exam equipment via the (PED 1)(FIG. 1D). The main control base (MCB 2) and universal adapter 11 (FIG. 3B)(FIG. 1D) may be used control any refractor, digital (phoropter 6 or liquid lens subjective refractor 6) (FIG. 3B) and/or digital vision chart 12 34 (FIG. 3B) via one or more software's 19 12 in the MCB 2 and a remote access software 23 (RAS) running in the background (FIG. 3B). The main control base may be a computing device using any operating system 24 Android, Windows, IOS or Linux and may run an emulating software, remote administration tool software and remote control software's to control a digital (phoropter 6 or liquid lens subjective refractor 6) and digital vision acuity chart 12 34 via indirect to direct connection and/or direct to direct connection if needed. (FIG. 3B) (FIG. 1F). The eye doctor 10 may have any portable electronic device (PED 1) (FIG. 4A) (FIG. 1F) with any operating system 24 Android, Windows, IOS or Linux, with an installed (RAT) software or (APP) (FIG. 1F).

The main control base may have a (RAT) application (FIG. 1B) and (phoropter 6 or liquid lens subjective refractor 6) operating software running (FIG. 3B) at the same time to be controlled by a controller 10 (eye doctor 10) (FIG. 3A) (FIG. 3B) from anywhere in the world 46. The support controller 10 (eye doctor 10) (FIG. 1A) may needs to have the (RAT) software (APP) open (FIG. 1A). The support controller 10 (eye doctor 10 needs to have the or RAT and/or one or more software's running on their PED. The method to use the PED to receive or send a request 16 to control the main control base (MCB 2) and/or the embedded or non embedded systems comprising a first and/or second computer system 7 with at one or more equipment control software's 7 13 21 34) by the controller 10 portable or personal electronic device (PED). (FIG. 1A) (FIG. 1B). The main purpose of the MCB 2 is direct control of one or more computer system and/or software's that controls at least one device, refractor, (digital phoropter or liquid lens subjective refractor 6) and/or vision acuity chart 34 via wired, USB 36 or Bluetooth 35 connection (FIG. 3B). The main control base may connect to the internet via Wi-Fi 3, or cellular wireless networks 3 connectivity (FIG. 3B) (FIG. 3A).

The (RAT) remote administration tool 23 mobile application or RAS software may run inside the existing operating system 24 of the (MCB 2) (FIG. 4B) (FIG. 3B). The controller 10 may be anyone with an electronic portable device (FIG. 1F) (FIG. 3A) with 4G, 5G, 6G or Wi-Fi 3 connectivity from anywhere in the world 46 with a cellphone signal or Wi-Fi 3. A portable electronic device (PED 1) such as a smartphone, tablet or laptop can control the main control base (MCB 2) via cellphone wireless networks, CWN LTE, 4G, 5G, 6G or Wi-Fi 3 (FIG. 1F). The MCB 2 can be remote-controlled over Internet protocol networks using an applet running on the communication device (FIG. 3B), and the support controller 10 (eye doctor 10) can control the (MCB 2) and/or first equipment computer control system by using a (RAT) application running on his or her portable or personal electronic device (smartphone, tablet, or Laptop) (FIG. 1F) When the patient, technician, optician, or doctor (FIG. 1B) sends a support request 16 to an on-demand (eye doctor 10) (FIG. 1A), (DR) he or she can accept 18 or decline 18 the request 16 for (RAT) interconnection 4.

If and when the (eye doctor 10) becomes a (controller 10) and accepts 18 the request 16, he or she must insert a user name and password 17 (FIG. 1A) for the office requesting 16 the support they wish to provide the support service. Each interconnecting session is encrypted, and can have two-factor authentication for security if needed. The (RAT or RAS) remotes administration tool and/or remote access software program installed within its system randomly generates a user name and password 17 authentication for the (eye doctor 10) controller 10 to be able to log in and connect to the MCB 2 (FIG. 1B) (FIG. 1A). This secures the peer-to-peer network (FIG. 1F) to control the (MCB 2) (FIG. 1F), which directly controls the digital (phoropter or liquid lens subjective refractor 6) control or digital (phoropter or liquid lens subjective refractor 6) software and vision chart 34 (FIG. 1F).

This random username and password 17 may facilitate a secure connection to any (eye doctor 10) who decides to accept 18 (FIG. 1F) (FIG. 3) to become a (support controller 10) to provide service with their portable electronic device. The controller 10 is indirectly controlling the digital (phoropter or liquid lens subjective refractor 6) (FIG. 1F) as the connection is made from the eye doctor 10 controller 10 (DPED 1) (FIG. 3A) (FIG. 3B) to the (MCB 2). By way of indirect to direct connection, the eye doctor 10 (DPED 1) may control the (MCB 2) which may aid in directly control the at least one medical device, device an/or robotic digital (phoropter or liquid lens subjective refractor 6), vision chart 34 (FIG. 3B) and equipment in the exam location 8 46. The (RAT or RAS) can use commercial software or non-commercial service to achieve its servers to middle-man to do the connection (FIG. 1F) and connection set-up, but most of the time, the relationship between client and server will be peer to peer (FIG. 1F) (controller 10 DPED 1 to MCB 2).

The controller 10 (eye doctor 10) may indirectly remotely operate the refractor, robotic digital (phoropter or liquid lens subjective refractor 6), near chart 32 29, digital (phoropter 6 or liquid lens subjective refractor 6) and vision chart 34, to refine a prescription (FIG. 4A) from a patient 5 behind the digital (phoropter 6 or liquid lens subjective refractor 6) (FIG. 4B). The patient 5 eyes can be tested for best visual acuity facilitating a proper prescription vision check (FIG. 3B). A patient 5 prescription may also be refined from using past existing prescription glasses or data 13 obtained in the office (FIG. 3B).

In a method where an assistant 38 may be in the exam room 46. An assistant 38 in the exam room 46 may read or import patient 5 auto-refractor 48 6, or keratometry readings result for both right and left eye (FIG. 4B)(FIG. 4A). The autorefractor system may also be operated remotely and used to import data 13 to MCB 2 or via the eye doctor 10 MCB 2 or by autonomous control. The assistant 38 or eye doctor may also view read existing glasses prescription by lensometry of both right and left eye (FIG. 4A). The eye doctor 10 may average out the lensometry reading and the automatic refractor 48 reading to acquire a patient starting point prescription in each eye individually using both right and left eye (FIG. 2A). This method may be the patient's 5 primary base refraction inputted into the digital (phoropter or liquid lens subjective refractor 6) (FIG. 3B) before remote prescription subjective refraction can be obtained by an eye doctor 10. The on-demand connection may use at least a combination connection using Bluetooth 35, long-distance Wi-Fi 3, 4G, 5G or 6G (FIG. 1F) (FIG. 3A) (FIG. 4A) (FIG. 4B) to achieve indirect to direct control 46.

The controller 10 (eye doctor 10) will be connected to the (MCB 2) via the (RAT). The on-demand Optometrist or Ophthalmologist (eye doctor 10) located anywhere in the world 46 may perform one or more refraction method including an indirect (RAT) objective, subjective refraction (IRATSR) and can communicate with the patient 5 via smartphone weblink connection. The secured video/audio 47 26, text or audio 47 26 connection may be HIPAA compliant encrypted video and voice or voice call (FIG. 4B) (FIG. 4A). For privacy, the patient 5 may also have the option of using over-the-ear headphones 37 (FIG. 4B) with a microphone 37 (FIG. 4B) to establish a clear voice connection with the eye doctor 10 (FIG. 4A). The support controller 10 (eye doctor 10) can also use portable headphones 37 with a microphone 37 to maintain clear communication with the patient 5 (FIG. 4A)(FIG. 1D). In some cases, an interactive smartphone application button selection system 22 may be used by the patient 5 to remotely select the lenses choices (FIG. 1D).

The Optometrist or Ophthalmologist (eye doctor 10) may ask the patient 5 which powered lenses or variation of dioptric powered liquid lens shape, focal length and/or (power) seem better aiding in refining the sphere 14, cylinder 14, and axis 14 of both eyes of the patient when viewing the smallest optotypes, patterns and/or shapes on the vision chart display 34 (FIG. 3B)(FIG. 1D). The eye doctor 10 may perform monocular subjective vision checks via the vision chart 34. This to each eyes of the patient to make the necessary adjustment to the prescription needed. The doctor 10 will verify patients 5 best visual acuities using a monocular method (one eye at a time) (FIG. 3B), binocular vision testing (both eyes together)' and binocular near vision to a patients 5. A last-minute monocular pinhole vision test may be used thru the robotic digital (phoropter or liquid lens subjective refractor 6) on each eye for distance validating if the prescription is correct. (FIG. 4B). This may be helpful with the refinement before releasing an eye glass prescription to the patient 5. The goal is to achieves the best-corrected distance visual acuity 40 with the best refine prescription (FIG. 5B).

Figure 5:
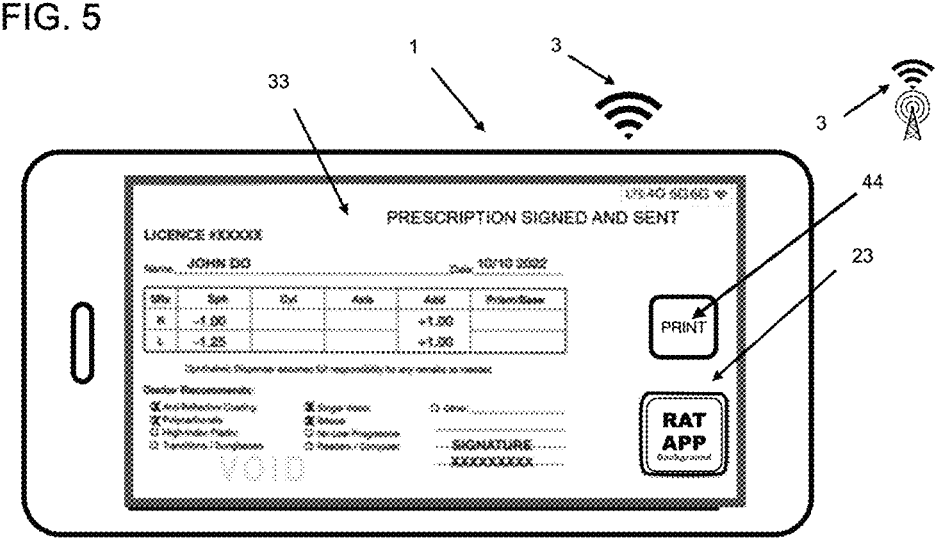
FIG. 5 Illustrates embodiment display of the eye doctor's portable or personal electronic device with a finalized prescription. Where the distance eye doctor can sign and send signed eyeglass prescription via finger to touch screen to the patient.

The eye doctor 10 may validate the patient 5 visual acuities and make the necessary correction to the refractive prescription. This will be done to acquire the patients' 5 best-corrected vision acuity in each eye (FIG. 5A) (FIG. 5B). The eye doctor 10 (controller 10) may view the chart 34 displayed via screen mirroring technology to his PED 1 via the RAT application (FIG. 5A) (FIG. 5B) (FIG. 5). A complete indirect (RAT) subjective refraction can be performed and a new eyeglasses prescription 33 may be generated after the refined subjective vision acuity check (FIG. 5B) (FIG. 5). After the refined indirect (RAT) subjective refraction is done the eye doctor 10 may send out the patient's 5 prescription via screenshot picture, printing 44 41 from the main control base, or email (FIG. 5A)(FIG. 5B).

What is claimed is:

1. A method to provide remote administration tool controlled refraction and vision examinations to patients, the method comprising:

establishing a secure connection between a Main Control Base (MCB) in one of: a mobile clinic and a non-mobile clinic and a Personal Electronic Device (PED) associated with an eye doctor, wherein the connection is established via end to end encrypted Health Insurance Portability and Accountability Act (HIPAA) internet network connection,
wherein the PED is configured to work on at least one of: a Remote Administration Tool (RAT) and a Remote Access Software (RAS) and includes at least one of: a laptop and a smartphone; wherein the MCB is configured to control a digital phoropter, vision chart and one or more medical devices and electronics devices in an exam room;

displaying a list of patients scheduled on at least one of: the MCB and the PED associated with a remote controller, wherein the remote controller includes at least one of: an assistant, an eye doctor, a health care professional, optometrist, ophthalmologist and medical professional;

receiving controlling instruction from the eye doctor to remotely allow a patient in the exam room and provide one or more instructions to the patient via the MCB, wherein the instruction are associated with at least one of: instructing the patient to scan a unique Quick Response (QR) code linked to an Uniform Resource Locator (URL) via a PED to establish connection with the PED of the remote controller, wherein the connection facilitates at least one of: exchange of encrypted audio, video and text between the patient and the remote controller, and facilitate the remote controller share screen and control the PED associated with the patient;

facilitating the remote controller to control the MCB remotely for controlling at least one of: a digital phoropter control, an exam chair, a phoropter near chart, a phoropter arm, a lens-meter software, an auto-refractor control, an exam room lights and a vision chart software; wherein controlling the exam chair includes adjusting vertical height and controlling the phoropter arm includes positioning a person to start a subjective refraction session;

reviewing via screen share and remote control the patient's EMR, lensometry data and autorefractor data to capture corrected refine patients distance and near subjective eyeglasses prescription; and signing the eyeglass prescription of the patient virtually, printing the eyeglass prescription and emailing the eyeglass prescription to the patient, wherein upon conclusion of remote subjective refraction session, the phoropter arm retracts, the exam chair lowers and the eye doctor is configured to answer one or more questions from the patient and provide one or more instructions to the patient associated with cleaning and leaving the clinic, wherein the patient may be followed up subsequently for another part of vision examination by an optometrist or ophthalmologist on site with a live eye doctor, or telemedicine health care provider based on requirements.

2. The method of claim 1, further comprises:
initiating one of: a smartphone application, a tablet application and laptop application to serve as a RAT for providing screen sharing and remote control to the eye doctors, wherein the controller is configured to receive two or more wireless communication protocols based on requirements;
receiving a secure interconnection from the controller associated with at least one of: the eye doctor and an assistant via at least one of: a commercial and non-commercial RAT software running in the application in the PED associated with the eye doctor portable electronic device and the MCB;
verifying all software on the MCB via one or more emulated screen are correctly functioning based on requirement;
verifying controlling of all software via encrypted RAT connections.

3. The method of claim 1, further comprises:
displaying a list of patients scheduled and geolocation of an exam room on the application running on the MCB remotely; and
displaying a list of selected patients from the PED of the eye doctor.

4. The method of claim 3, further comprising:
receiving data from at least one of: a virtual and a live assistant to access the selected patient from the patient list via the MCB;
verifying sharing the patient list on online medical appointment booking service via at least one of: the virtual and the live assistant for medical providers based on requirements; and
verifying correct running of all software inside the MCB and a software running inside an emulator inside the MCB and are gathering data and sending data.

5. The method of claim 1, further comprising:
initiating the eye doctor connection and control to the MCB to direct the MCB via visual text or voice prerecorded text to speech to instruct the patient to use PED to scan unique QR code and link the URL to establish virtual eye doctor connection, wherein the link URL connection is via the eye doctor and patient PED and via secondary screen sharing tool based on requirement;
verifying opening of the link by the patient for manual selection of lenses via at least two buttons choice system, wherein each number corresponds to a lens during the exam, and the eye doctor is configured to facilitate the patient to control the digital phoropter based on requirements, wherein the MCB is configured to instruct the patient about choosing selection lens in the subjective refraction.

6. The method of claim 1, further comprises:
initiating the eye doctor and virtual assistant control to view connection with the MCB remotely; and
viewing and controlling a secure password encrypted patients data, a pre-testing and a patient electronic medical record data via screen sharing, wherein viewing the data is performed at least on the prior and same day.

7. The method of claim 1, further comprises
controlling a vision chart by the main control base software, controlling an MCB vision chart software via RAT screen share and remote control with the controller personal electronic device RAT mobile application, wherein the vision chart can also work as a color vision testing device to remotely change color plates to gather color vision testing, wherein all connection from the MCB softwares to a vision chart display may be via broadband cellular network technology, infrared, Bluetooth, or WiFi depending on the system used and can be controlled from anywhere in the world.

8. The method of claim 1, further comprises:
controlling the MCB to remotely control robotic medical and non medical equipment in the exam room;
controlling the MCB to control the digital phoropter for performing a distance and near subjective refraction via the RAT inside a smartphone application on the PED associated with the eye doctors.

9. The method of claim 1, further comprises:
controlling the MCB via RAT screen share and remote control to manipulate office robotic equipment and lights remotely and navigating the digital phoropter control and the vision chart control to start subjective vision refraction session.

10. The method of claim 1, further comprises:
transmitting automatic lens-meter readings, and auto-refractor results on the MCB remotely via at least one of: RAT screen share, control, automatic transfer Bluetooth, emulators with screen share capabilities, wherein the emulator is enabled a computer system to clone another computer system.

11. The method of claim 10, further comprises
using the patient data from an automatic lensometry reading from patients right and left eye old glasses prescription;
wherein the information is gathered by facilitating the patient to place his or her eye glasses on a specific automatic semi-autonomous lens-meter machine; wherein the machine can read the glasses prescription by at least one of: automatically and by the press of a button; and wherein the results are automatically sent to the MCB, received via the RAT screen share, by emulator screen sharing.

12. The method of claim 11, further comprises:
gathering and recording the auto-refractor results from past technician evaluations and the remote auto-refractor; and
sending both readings automatically on the MCB via an application through Bluetooth, wired, WiFi, RAT screen share, remote control and emulators screen sharing
averaging both eyes automatic lensometry readings and auto-refractor readings to get a starting point subjective refraction prescription lenses on the digital phoropter for the right and left eye lenses; and
inputting the information to the MCB to lenses for automatically changing to the averaged prescription reading calculated.

13. The method of claim 1, further comprises:
transmitting, subsequent to adjusting the patient properly and remotely situating the robotic phoropter arm, a tentative prescription to the digital phoropter and adjusting the patient behind the automated phoropter for beginning the session;

initiating an indirect to direct subjective refraction;

refining each eyes lens prescription individually, starting with refining at least one of: sphere, cylinder and axis of each eye, wherein during the refining the patient is instructed to select buttons corresponding to the lens via an application, verbal and visual sign language;

instructing the patient to choose between dual options for lenses with a patient smartphone application based on requirement;

displaying the results;

displaying the results of the patients selection via application with a secondary device answering based on user selection;

changing the lenses based on the user selection, wherein the patient is configured to send a response to the eye doctor about accuracy of the lens; and wherein the patient is facilitated with an option of a verbal communication for choosing the lens via RAT screen share and remote control.

14. The method of claim 3, further comprises:

refining a prescription of a right and a left eye independently for sphere power, cylinder power, and axis via RAT screen share and remote control; and performing at least one of: a red-green chromatic aberration test, a binocular balance test, monocular vision test and binocular test to acquire an acuity for patients final prescription, wherein the eye doctor performs, anytime during the exam, a monocular lens sun burst dial and a clock dial test via a vision chart to verify astigmatic correction, and a pinhole test to find optimal VA.

15. The method of claim 1, further comprises:

starting a near subjective refraction by moving a near robotic chart down, such that a near vision chart is visible to the patient, wherein an accommodative test is performed via remote means to acquire add appropriate power for presbyopic patient;

retracting the near chart when the testing and add power is found by the doctor via an application on the MCB.

16. The method of claim 1, further comprises:

delegating view and control of patients' electronic medical record data via a RAT screen sharing and control;

wherein a first eye doctor delegates secondary connection to a secondary eye doctor, wherein the secondary doctor is configured to view and control the MCB software installed and running in the MCU; and wherein the first or secondary eye doctor is configured to view, control and explain at least one of: the patients electronic medical record data, retinal health images, or external ocular health pictures of all the ocular parts via the PED associated with the first or secondary eye doctor.

17. The method of claim 1, further comprising:

providing and delegating service to other medical doctors and eye doctors via secure encrypted connection; and determining fees and terms associated with the eye doctors providing HIPAA compliant encrypted RAT refractions services to patients; wherein a mobile application and the software facilitates setting a personal profile with a name, phone number, state license number, other information and payment preference, wherein the payment preference includes at least one of: a credit card, e-commerce payment system, cryptocurrency address, and cash.

18. A electronic system to provide remote administration vision examination and refraction services to patients, the system comprising:

a Main Control Base (MCB) coupled to at least a portion of one or more electronic devices; and wherein the one and more electronic devices and one or more user interfaces are emulated and controllable by the at least one MCB computer system; and wherein the one or more electronic devices comprises one or more softwares and a medical devices control software configured to control one or more medical devices to be used to perform at least one vision examination for a patient;

a Personal Electronic Device (PED) associated with an eye doctor; and one or more PED associated with the one or more patients; wherein the MCB is configured to:

establish a internet secure connection between the MCB and the PED associated with an eye doctor, wherein the connection is established via end to end encrypted Health Insurance Portability and Accountability Act (HIPAA), wherein the PED is configured to work on at least one of: a Remote Administration Tool (RAT) and a Remote Access Software (RAS) and includes at least one of: a laptop and a smartphone; and wherein the MCB is configured to control a digital phoropter, vision chart and one or more equipment's in an exam room;

wherein the exam room comprises at least one of: a mobile clinic and a non-mobile clinic; and wherein a mean of controlling the MCB from a PED comprises control from any geolocation in the planet;

display a list of patients scheduled at least on one of: the MCB and the PED associated with the eye doctor;

receive controlling instruction from the eye doctor to remotely open a door of the exam room to allow a patient in and provide one or more instructions to the patient via the MCB, wherein the instruction are associated with at least one of: instructing the patient to scan a unique Quick Response (QR) code linked to an Uniform Resource Locator (URL) via a PED associated with the patient to establish connection with the PED of the eye doctor, wherein the connection facilitates at least one of: exchange of encrypted audio, video and text between the patient and the eye doctor, and facilitate the eye doctor share screen and control the PED associated with the patient;

facilitate the eye doctor to control the MCB remotely for controlling at least one of: a door lock, a digital phoropter control, an exam chair, a robotic phoropter near chart, a robotic phoropter arm, a lens-meter software, an auto-refractor control, an exam room lights and a vision chart software; wherein controlling the exam chair includes adjusting vertical height and controlling the robotic phoropter arm includes positioning a person to start a subjective refraction session;

review patient's EMR, lensometry data and autorefractor data to capture corrected refine patients distance and near subjective eyeglasses prescription; and sign the eyeglass prescription of the patient virtually, printing the eyeglass prescription and emailing the eyeglass prescription to a PED associate with the patient, wherein upon conclusion of remote subjective refraction session, the phoropter arm retracts, the exam chair lowers and the eye doctor is configured to answer one or more questions from the patient and provide one or more instructions to the patient associated with cleaning and leaving the clinic, wherein the patient may be followed up subsequently for another part of eye health examination by an optometrist or ophthalmologist on site with a live eye doctor, or telemedicine doctor based on requirements.

19. An electronic system to provide remote administration tool vision examination and subjective refraction services to examinee using an MCB computing device, the system comprising:
an electronic main computer base (MCB) positioned at a geolocation, and comprising:
an operating system;
a user interface;
an adapter
a computer emulator; and
a Remote administration tool (RAT);
wherein the Main Control Base (MCB) is coupled to at least a portion of one or more electronic devices; and
wherein the one or more electronic devices including the one or more user interfaces emulated and controllable by an MCB; and
wherein the one or more electronic devices comprises one or more software's and a medical devices control interfaces configured to receive instruction for controlling for operating the one or more medical devices by an user to administer one or more vision examination for a examinee; and
one or more Portable Electronic Device (PED) associated with an user; and
one or more PED associated with the one or more examinee; and
wherein in the examinee includes at least one of: a patient, customer, and any human person; and
wherein the user includes at least one of: an assistant, an eye doctor, a health care professional, optometrist, ophthalmologist, and healthcare provider; and
wherein the user comprises control to the MCB system from any geolocation in the planet;
wherein the MCB is configured to:
establish a internet secure connection between the MCB and the PED associated with an user, wherein the connection is established via end to end encrypted Health Insurance Portability and Accountability Act (HIPAA) RAT,
wherein the PED is configured to work on at least one of: a Remote Administration Tool (RAT) and a Remote Access Software (RAS) and includes at least one of: a tablet, a laptop and a smartphone; and
wherein the MCB is configured to control a digital phoropter, vision chart and one or more devices and equipment's in an exam location;
wherein the exam location comprises at least one of: an exam area, an exam room, a mobile clinic and a non-mobile clinic; and wherein a mean of controlling the MCB from a PED comprises control from any geolocation in the planet;
display a list of persons scheduled at least on one of: the MCB and the PED associated with the user;
receive controlling instruction from the user to allow a examinee in and provide one or more instructions to the examinee via the MCB, wherein the instruction are associated with at least one of: instructing the examinee to scan a unique Quick Response (QR) code linked to an Uniform Resource Locator (URL) via a PED associated with the examinee to establish connection with the PED of the user, wherein the connection facilitates at least one of: exchange of encrypted audio, video and text between the examinee and the user, and facilitate the user share screen and control the PED associated with the examinee; and
facilitate the user to screen view and control the MCB remotely for controlling at least one of: a door lock, a digital phoropter control, an exam chair, a robotic phoropter near chart, a robotic phoropter arm, a lensmeter software, an auto-refractor control, an exam room lights and a vision chart software; wherein controlling the exam chair includes adjusting vertical height and controlling the robotic phoropter arm remotely includes positioning a examinee to start a subjective refraction session;
review and control the examinee's EMR data, lensometry data and autorefractor data to capture corrected refine examinee distance and near subjective eyeglasses prescription; and
control and view the main control base user interface remotely to administer a vision examination and subjective refraction to a examinee;
wherein the vision examination comprises remotely controlling the electronic devices that control the autorefractor, pupilometer and one or more equipment to administer and review pre-fraction data; and
Control the electronic devices that control the digital phoropter, vision chart and one or more devices;
acquire the best corrected refinement examinee's distance and near subjective eyeglasses prescription for the examinee; and
wherein eyeglasses prescription comprises sphere, cylinder and axis of examinee's both eyes; and
sign the eyeglass prescription of the examinee virtually, printing the eyeglass prescription and emailing the eyeglass prescription to a PED associate with the examinee.

20. The electronic system of claim 19, wherein the PED associated with the user includes a mobile application and software further configured to remotely access, remote control, and remote screen view one or more medical devices interfaces, and non-medical devices interfaces and electronic medical record user interface, to administer a real time remote controlled vision examination to an examinee from any location in the planet without the need of an local technician to operate the equipment.

* * * * *